US00PP36385P2

(12) United States Plant Patent
Hatterman-Valenti et al.

(10) Patent No.: US PP36,385 P2
(45) Date of Patent: Jan. 14, 2025

(54) GRAPE PLANT NAMED 'ND054.27'

(50) Latin Name: ***Vitis spp.* hybrid**
Varietal Denomination: ND054.27

(71) Applicant: NDSU RESEARCH FOUNDATION, Fargo, ND (US)

(72) Inventors: Harlene M. Hatterman-Valenti, Fargo, ND (US); John E. Stenger, Fargo, ND (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 0 days.

(21) Appl. No.: 18/417,846

(22) Filed: Jan. 19, 2024

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./205, 206, 207
See application file for complete search history.

(56) References Cited

U.S. PATENT DOCUMENTS

PP16,478 P3 4/2006 Luby et al.

*Primary Examiner* — Susan McCormick Ewoldt
(74) *Attorney, Agent, or Firm* — McKee, Voorhees & Sease, PLC

(57) ABSTRACT

The grape plant cultivar 'ND054.27' is a white wine grape which exhibits excellent yield and superior cold hardiness and disease resistance.

3 Drawing Sheets

STATEMENT REGARDING FEDERALLY SPONSORED RESEARCH

This invention was made with government support under NI18HMFPXXXXG008, NI19HMFPXXXXG008, NI22HMFPXXXXG015, NI21HMFPXXXXG018, and NI20HMFPXXXXG005 awarded by the United States Department of Agriculture's National Institute for Food and Agriculture (USDA-NIFA) and AM200100XXXXG063 awarded by the United States Department of Agriculture's Agricultural Marketing Service (USDA-AMS). The government has certain rights in the invention.

Botanical designation:

Genus and species: *Vitis* spp. hybrid.

Variety denomination: The new plant has the varietal denomination 'ND054.27'.

BACKGROUND

Most grape varieties used for production of high-quality wines around the world are of the species *Vitis vinifera*. These *V. vinifera* varieties, when cultivated in northern regions of the United States with a continental climate, are often subject to serious injury or death from low temperatures during winter. Although several wild *Vitis* species occur in colder regions of North America and eastern Asia, the wine made from these species generally has serious defects. Thus, there is a need for grape varieties that are winter hardy yet produce fruit capable of yielding high quality wine.

BRIEF SUMMARY

'ND054.27' is a variety of grape (*Vitis* hybrid) suitable for white wine production and is well adapted to the Upper Midwest climate of the United States. 'ND054.27' is extremely high yielding and exhibits a high level of cold hardiness. 'ND054.27' showed limited cold temperature dieback (winter injury) in comparison to the cold hardy gris wine grape 'Frontenac Gris' (U.S. Plant Pat. No. 16,478). The fruit of 'ND054.27' produces a good quality, well balanced wine with notes of apple, melon, watermelon, pear, and citrus. 'ND054.27' exhibits good disease resistance, showing low susceptibility to powdery mildew (*Uncinula necator*), downy mildew (*Plasmopara viticola*), black rot (*Guignardia bidwellii*), and foliar phylloxera (*Daktulosphaira vitifoliae*).

'ND054.27' originated from a hand-pollinated cross of 'Frontenac Gris' (female parent) and 'Adalmiina' (male parent, not patented) made in 2011. Asexual propagation of the new cultivar was accomplished by rooting hardwood cuttings in 2015 in Fargo, ND. Asexual propagation of the cultivar by rooted hardwood cuttings has determined that the characteristics are stable and true to type in successive generations.

DETAILED BOTANICAL DESCRIPTION

Figure 1:
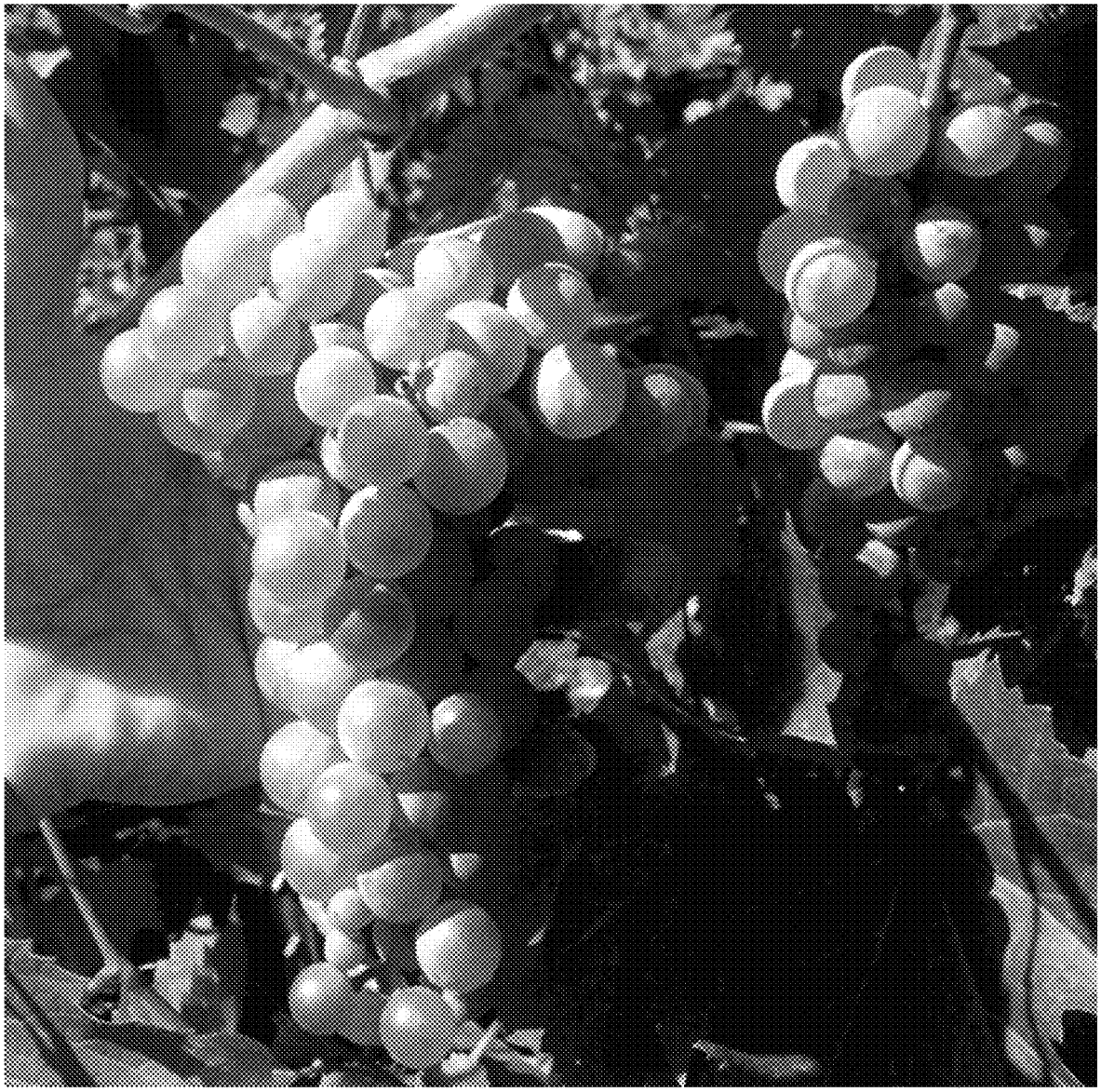
FIG. 1 is a photograph taken in 2014 of a 'ND054.27' fruit cluster on three-year-old vines grown in Fargo, ND.
Figure 2:
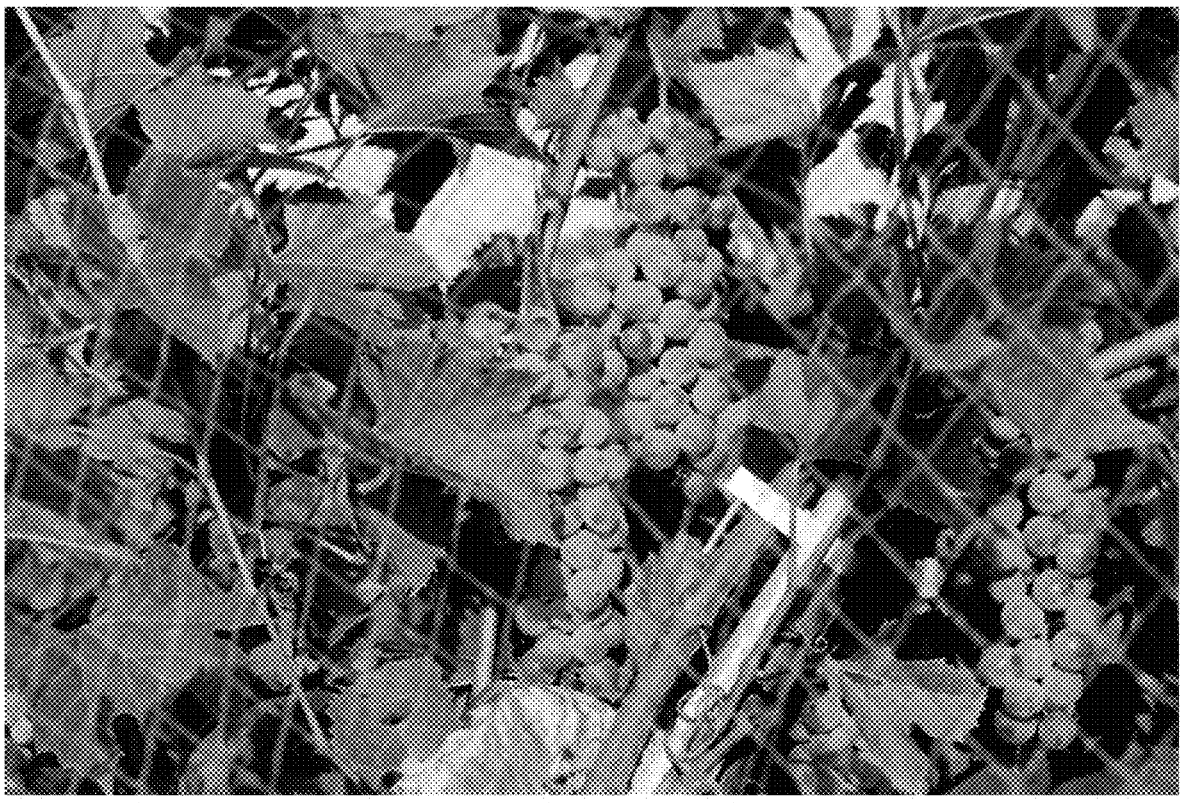
FIG. 2 is a photograph taken in 2018 of a 'ND054.27' fruit cluster on two-year-old vines grown near Absaraka, ND.
Figure 3A:
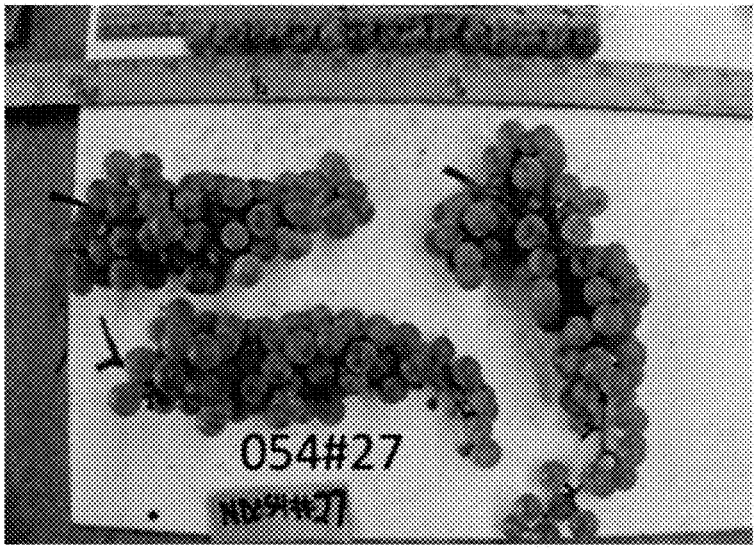
FIGS. 3A and 3B are photographs taken in 2014 of harvested 'ND054.27' fruit from three- year-old vines grown in Fargo, ND.
Figure 3B:
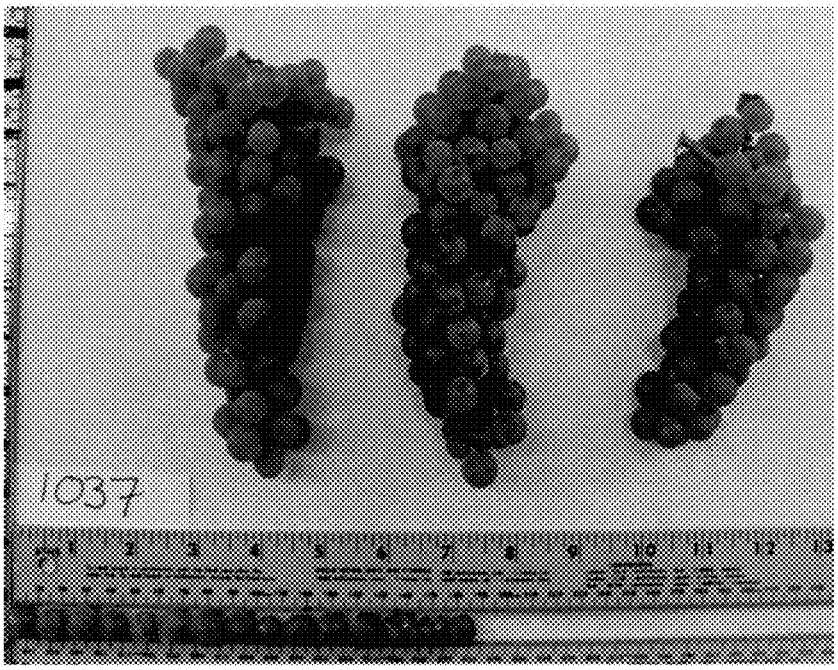

'ND054.27' differs from female parent, 'Frontenac Gris', in that ND054.27 tended to have larger more compact clusters with larger berries. ND054.27 ripened berries classified as white and were not gris. ND054.27 berries ripened to lower brix and titratable acidity. Data collected in 2018 near Absaraka, ND reinforced observations where both (cultivars) were growing but not in the same trial with ND054.27 having 40% greater cluster weight and 124% greater berry weight.

'ND054.27' differs from male parent, 'Adalmiina', in that ND054.27 tended to have a more compact cluster ripening later and to lower brix. ND054.27 clusters were less prone to shatter. Overall, ND054.27 was less *V. labrusca* in appearance with stems and leaves more similar to its mother Frontenac Gris. Data collected in 2018 near Absaraka, ND indicated that ND054.27 was more cold hardy than 'Adalmiina', which had only four of 16 vines that produced fruit. ND054.27 clusters weighed 254% more than 'Adalmiina' and berry weight was 22% greater, but cluster weight may have been compromised from the cold temperature injury.

The following is a detailed botanical description of the new variety of grape plant, its flowers, fruit, foliage etc. as based on observations of various aged specimens grown in Absaraka, ND and Fargo, ND over the 2016-2021 growing seasons. All color references are taken from The Royal Horticultural Society (R.H.S.) Colour Chart, 5th Edition.

TABLE 1

| Trait | Value |
|---|---|
| Botanical classification: | Cultivar of *Vitis* with ancestry from several species including, *V. vinifera*, *V. riparia*, and *V. labrusca*. |
| Parentage: | 'Frontenac gris' (female), 'Adalmiina' (male). |
| Mature canes: | The observations are the means of 10 canes observed from the 2019 to 2021 growing seasons. |
| Color of canes. | Between 175B and 167B |
| Length of canes. | 1.31 m (0.58-2.45 m) |
| Diameter of canes. | 7.1 mm (stdev 1.4 mm) |
| Internode length | 49.4 mm (stdev 24.2 mm) |
| Lenticels | Present, <1 mm in length, color 203A. |
| Cane cross-section shape. | Circular to ovate. |
| Density of hairs on mature cane. | Absent. |
| Tendril pattern on shoot | 2,0, 2,0; two nodes with tendrils followed by one node without. |
| Tendrils forked | Yes |
| Tendril texture | Striated |
| Tendril color | 144A |
| Bud width | 3.5 mm (stdev 1.2 mm) |
| Bud length | 5.2 mm (stdev 1.6 mm) |
| Bud shape | Triangular. |
| Bud color | Between 173A and 166A. |
| Trunk: | The observations of trunk characteristics presented are from the 2019 growing season. |
| Bark texture | Somewhat flaky, small vertical segments below 5 mm in width and length. |
| Bark color. | Light sections of 161 A with striated darker sections of N170A |
| Mature leaves | Ten representative mature leaves were collected from above the cluster at each growing location. The leaves were pressed and dried for analysis. The values presented are means from leaves collected in Absaraka, ND and Fargo, ND in 2020. Descriptors of mature leaves relate to OIV descriptor list for grape varieties and *Vitis* species (OIV, International Organisation of Vine and Wine, Technical document ). |
| Length of blade. | 13 cm (9.1-15.9). |
| Width of blade. | 15.4 cm (9.6-20.0). |
| Shape of blade. | Cuneiform, wedge-shaped. |

TABLE 1-continued

| Trait | Value |
|---|---|
| Number of lobes. | Three to five. |
| Blade margins. | Incised into three to five lobes. |
| Length of primary (midrib) vein N1 from the tip of the blade to the petiole sinus. | 130 mm (stdev 26). |
| Length of vein N2 from the tip of the first major lobe of the blade to the petiole sinus. | 117 mm (stdev 27). |
| Length of vein N3 from the tip of the second major lobe of the blade to the petiole sinus. | 82 mm (stdev 20). |
| Length of vein N4 from the tip of the third major lob of the blade to where it joins the vein measured in N3. | 43 mm (stdev 11). |
| Length of vein N5 from the tip of the first tooth proximal to the petiole sinus to where it joins the vein measured in N4. | 19.7 (stdev 5.5). |
| Length of N2 teeth. | 13.8 mm (stdev 4.8). |
| Width of N2 teeth. | 13.1 mm (stdev 4.3). |
| Length/width ratio of N2 teeth. | 1.05 |
| Length of N4 teeth. | 6.4 mm (stdev 2.2) |
| Width of N4 teeth. | 9.6 mm (stdev 3.5) |
| Length/width ratio of N4 teeth. | 0.67 |
| Shape of teeth. | Both sides typically straight, occassionally convex. |
| Shape of petiolar sinus. | Very wide open. |
| Shape of base of petiolar sinus. | Brace shaped. |
| Depth of petiolar sinus. | 31.1 mm (stdev 10.2) |
| Width of petiolar sinus. | 49.3 mm (stdev 11.5) |
| Petiole. | Diameter 2.5 mm; length 94.3 mm (stdev 25.7). |
| Shape of upper sinuses. | U-shaped. |
| Shape of base of upper sinuses. | None. |
| Pubescence on adaxial surface. | Slight. |
| Pubescence on abaxial surface. | Slight |
| Color of adaxial leaf surface. | Between N137A and 135A. |
| Color of abaxial leaf surface. | 143C |
| Color of leaf petiole. | 1C to 1D with pigmentation of 45B. |
| Center lobe size. | Length 5.7 cm; width 6.8 cm. |
| Lateral lobe size. | Length 4.2 cm; width 3.8 cm. |
| Basal lobe size. | Length 1.8 cm; width 2.0 cm. |
| Young shoots: | |
| Form of shoot tip. | Mainly open. |
| Density of prostrate hairs on tip. | Sparse |
| Density of erect hairs on tip. | Dense, tomentose |
| Petiole pigmentation | 144A |
| Shoot attitude. | Semi-procumbent |
| Shoot pigmentation (internodes and nodes). | N974B on sun-exposed side, 143C on bottom |
| Young leaves. | Adaxial surface 144C |
| Flowers: | The observations of flower characteristics presented are from the 2019 growing season. |
| Fragrances. | Moderately fragrant. |
| Mean time of flowering. | 06/01 (05/28-06/8) when grown near Fargo, ND |
| Color of calyx. | 149A. |
| Sepal number. | 5 sepals fused into a continuous calyx. |
| Calyx shape. | Ring shaped |
| Calyx size. | 1.76 mm in length (1.4-2.3); 2.23 mm in diameter (1.8-3.3) |
| Calyx apex. | Fused to ovary. |
| Calyx base. | Fused to pedicel. |
| Nectary. | Diameter; length; color 153D. |
| Calyx surface. | Glabrous. |
| Petals. | 5 petals fused in calyptra. |
| Color of Petal. | Between 149A and N144B |
| Shape of cluster. | Conical to short conical, typically with one shoulder. |
| Size of cluster. | 11.7 cm long; 5.3 cm wide. |
| Number of flowers. | Average of 125 with up to 47 on wings if present. |

TABLE 1-continued

| Trait | Value |
|---|---|
| Flower buds. | Length 4.7 mm (stdev 1.1); width 1.8 mm (stdev 0.3). |
| Size of individual entire flower. | 4.7 mm in height; 1.7 mm wide. |
| Pollen fertility. | Fertile based on selfing and use as parent in controlled crosses. |
| Reproductive organs. | Fully developed stamens and gynoecium. |
| Color of stamen. | Anther: 20 B; filament: 160D. |
| Stamen number. | Average of 5. |
| Filament length. | length 3.6 mm (stdev 1.1). |
| Anther. | Length <1 mm. |
| Pollen quantity and color. | Abundant, color between 13B and 15B. |
| Pistil. | 1 pistil present; ovary length 1.7 mm; pstil width 1.3 mm, urn-shaped. |
| Pedicel | 2.5 mm length and <1 mm width, surface glabrous. |
| Peduncle. | Peduncle length to base of cluster 15.5 cm (stdev 6.4 cm); peduncle width 3.1 cm (stdev 1.1 cm). |
| Peduncle color. | Between 149A and 150A. |
| Fruit. | Values represent the means (with ranges in parentheses) for fruit harvested over five growing seasons, 2016-2020. Specific color parameters and seed parameters were recorded on fruit and seed from the 2019 growing season. |
| Cluster length. | 15.3 cm (10.2-21.0) |
| Cluster diameter. | 8.2 cm (6.1-11.2) |
| Cluster weight. | 125 g (65-188 g) |
| Cluster density. | Medium, based on Trait 204 of the International Organisation of Vine and Wine (OIV) Descriptor List for grape varieties and Vitis species, $2^{nd}$ Edition. |
| Berry weight. | 2.52 g (2.10-3.12 g) |
| Berry length. | 1.72 cm. |
| Berry diameter at equator. | 1.66 cm. |
| Berry shape. | Roundish. |
| Berry cross-section. | Circular. |
| Berry, color of skin. | 149B to 149A ripening to a more golden 154A to 154B. |
| Berry, color of flesh. | 149D. |
| Berry firmness. | Slightly firm. |
| Berry, particular flavor. | Neutral to slightly fruity, *V. labrusca* characteristic flavors develop when fruit becomes over-ripe. |
| Length of pedicel. | 5.3 mm (4.5 to 6.3 mm) |
| Pedicel diameter. | 1.4 mm (0.9 to 1.8 mm) |
| Pedicel color. | 142D. |

TABLE 1-continued

| Trait | Value |
|---|---|
| Berry, separation from pedicel. | Difficult. |
| Berry, presence of seeds. | Fully developed. |
| Seed number/berry. | 3.1 (1-4) |
| Seed length. | average 6.025 mm, SD 0.437 mm |
| Seed width. | average 3.836 mm, SD 0.264 mm |
| Seed length/width ratio. | 1.57 |
| Seed weight. | 0.0346 grams |
| Seed color. | 165A |
| Fruit: | Values represent the means (with ranges in parentheses) for fruit harvested over five growing seasons, 2016-2020. |
| Harvest date. | 09/06 (08/24 - 09/24) |
| Brix. | 18.1 (15.5-22.2) |
| pH. | 3.25 (3.06-3.42) |
| Titratable acidity. | 11.1 (9.0-15.5) g/liter. |
| Vineyard performance: | Descriptions are based on field observations made over four years (2017-2020). |
| Susceptibility to powdery mildew (*Uncinula necator*). | Low. |
| Susceptibility to downy mildew (*Plasmopara viticola*). | Low. |
| Susceptibility to black rot (*Guignardia bidwellii*). | Low. |
| Susceptibility to grey mold (*Botrytis cinerea*). | None observed. |
| Susceptibility to foliar phylloxera (*Daktulosphaira vitifoliae*). | Low. |
| Susceptibility to crown gall (*Agrobacterium tumefaciens*). | None observed. |
| Susceptibility to phenoxy herbicide drift. | Low. |
| Berry splitting. | None observed. |
| Berry shelling. | None observed. |
| Vigor level. | Moderate. |
| Winter hardiness. | Moderate-high. |
| Wood ripening. | Good. |
| Productivity. | Average yield between 8-20 lbs (3.6-9.0 kg)/plant, based on pruning, spacing, and location |

I claim:

1. A new and distinct grape plant cultivar designated 'ND054.27' substantially as described and illustrated herein.

* * * * *